(12) United States Patent  
Beimler et al.

(10) Patent No.: US 7,938,578 B2
(45) Date of Patent: May 10, 2011

(54) POSITIONING OF AN X-RAY APPARATUS

(75) Inventors: Franz Beimler, Weiden (DE); Joachim Trummer, Vilseck (DE); Dieter Wöhrl, Kemnath (DE)

(73) Assignee: Siemens Aktiengesellschaft, Munich (DE)

( * ) Notice: Subject to any disclaimer, the term of this patent is extended or adjusted under 35 U.S.C. 154(b) by 126 days.

(21) Appl. No.: 12/470,295

(22) Filed: May 21, 2009

(65) Prior Publication Data

US 2009/0296891 A1  Dec. 3, 2009

(30) Foreign Application Priority Data

May 27, 2008 (DE) .......................... 10 2008 025 242

(51) Int. Cl.
*H05G 1/02* (2006.01)
(52) U.S. Cl. .......................... 378/189; 378/196; 378/197
(58) Field of Classification Search .................. 378/189, 378/196, 197
See application file for complete search history.

(56) References Cited

U.S. PATENT DOCUMENTS

| 3,927,326 | A | * | 12/1975 | Kunne et al. | .................. | 378/179 |
|---|---|---|---|---|---|---|
| 4,618,133 | A | | 10/1986 | Siczek et al. | | |
| 5,014,292 | A | * | 5/1991 | Siczek et al. | .................. | 378/196 |
| 5,386,453 | A | * | 1/1995 | Harrawood et al. | .......... | 378/196 |
| 5,822,814 | A | * | 10/1998 | Van der Ende | .................. | 5/601 |
| 5,870,450 | A | * | 2/1999 | Khutoryansky et al. | ...... | 378/197 |
| 6,095,685 | A | * | 8/2000 | Tamura | .......................... | 378/196 |
| 6,152,598 | A | * | 11/2000 | Tomisaki et al. | .............. | 378/209 |
| 6,282,264 | B1 | * | 8/2001 | Smith et al. | ..................... | 378/189 |
| 6,364,525 | B1 | * | 4/2002 | Mellstrom et al. | ............ | 378/197 |
| 6,382,832 | B1 | * | 5/2002 | Schwieker et al. | ........... | 378/196 |
| 6,513,973 | B1 | * | 2/2003 | Fadler et al. | ................... | 378/190 |
| 6,789,940 | B2 | * | 9/2004 | Meyer et al. | ................... | 378/196 |
| 7,634,308 | B2 | * | 12/2009 | Ogawa | .......................... | 600/431 |

FOREIGN PATENT DOCUMENTS

DE  199 27 756 C5  11/2006

OTHER PUBLICATIONS

German Office Action dated Nov. 12, 2008 for DE 2008 025 242.5 with English translation.

* cited by examiner

*Primary Examiner* — Allen C. Ho
(74) *Attorney, Agent, or Firm* — Lempia Summerfield Katz LLC

(57) ABSTRACT

An x-ray apparatus is provided. The x-ray apparatus includes a patient support supported on a support unit in such a manner that it can be repositioned by way of a support arm and an x-ray detector likewise supported on the support arm, embodied in particular as a solid-state detector. The x-ray detector can be moved perpendicular to the patient support by way of a retaining column of a repositioning mechanism and can be rotated relative to the patient support about a first longitudinal axis extending in a longitudinal direction of the patient support. To increase the flexibility of the x-ray apparatus, the x-ray detector is supported in such a manner that it can be rotated relative to the patient support about a transverse axis extending in a transverse direction of the patient support.

13 Claims, 4 Drawing Sheets

POSITIONING OF AN X-RAY APPARATUS

This patent document claims the benefit of DE 10 2008 025 242.5 filed May 27, 2008, which is hereby incorporated by reference.

BACKGROUND

The present embodiments relate to positioning of an x-ray apparatus.

DE 199 27 756 C5 describes an x-ray diagnosis device. The x-ray diagnosis device includes a support plate for a patient that can be repositioned on a base. A solid-state detector is disposed on a gallows frame, which is supported on the support plate in a movable manner. The solid-state detector can be moved in all three spatial directions in relation to the support plate by way of the gallows frame. The solid-state detector is also supported on the gallows frame in such a manner that it can be swiveled about a rotation axis, which extends in a longitudinal direction of the support plate.

SUMMARY AND DESCRIPTION

The present embodiments may obviate one or more of the limitations or drawbacks inherent in the related art. For example, the present embodiments may extend the repositioning options for an x-ray apparatus.

The x-ray apparatus may include a patient support (e.g., a couch) that is supported on a support unit in a movable manner and an x-ray detector. The x-ray detector may be a solid-state detector. The x-ray detector may be moved by way of a retaining column perpendicular to the patient support and may be rotated, relative to the patient support, about a first longitudinal axis extending in the longitudinal direction of the patient support.

In one embodiment, an x-ray apparatus includes a patient support and an x-ray detector. The patient support may be supported on a support unit in such a manner that it can be repositioned by way of a support arm. The x-ray detector may be supported on the support arm. The x-ray detector may be a solid-state detector. The x-ray detector may be moved by a retaining column of a repositioning mechanism for the x-ray detector perpendicular to the patient support and rotated relative to the patient support about a first longitudinal axis extending in the longitudinal direction of the patient support. The x-ray detector may be supported in such a manner that it can be rotated relative to the patient support about a transverse axis extending in a transverse direction of the patient support.

The freedom of movement of the x-ray apparatus is increased by providing a further rotation axis for the x-ray detector. Rotatability about the first longitudinal axis may include moving the x-ray detector from a horizontal position above the patient support into a lateral position to the side of the patient support. During this process, recordings of the patient may be taken from a number of directions using the same detector, without having to move the patient. The additional rotation axis extending in a transverse direction in combination with a swiveling movement of the patient support provides a further recording position, in which examinations can be carried out on the standing patient. The patient support may be swiveled and raised, so that the patient support stands in a vertical position. As a result, the patient support may form a type of wall. The patient support is not required for the recording. With the x-ray apparatus, the x-ray detector, which can now be rotated about at least the one longitudinal axis and about a transverse axis, can be moved into a horizontal position, so that recordings can be taken of extremities positioned on the detector.

The x-ray apparatus may be used for fluoroscopy recordings of a prone patient and for static recordings, for example, of the bones of the patient. Fluoroscopy recordings include a continuous observation of processes in the body of the patient by x-ray radiation, for example, the act of swallowing. The additional rotation axis, with the aid of which the x-ray detector may be moved into a number of recording positions, therefore allows further medical applications of the x-ray device.

The x-ray detector may be moved along a curved path about the first longitudinal axis. During this process, the x-ray detector executes an orbital rotational movement about the first longitudinal axis running between the x-ray detector and the patient support. Compared with the known prior art the orbital rotational movement results in a simplified movement sequence, in which the x-ray detector at least partially circles a patient positioned on the patient support. The combined interaction of at least two linear displacements of the x-ray detector, which allows rotatability about the first longitudinal axis, is replaced in the proposed x-ray apparatus by a single rotational movement, which is simpler to execute and control.

The repositioning movement about the first longitudinal axis along a curved path may be provided irrespective of the arrangement of the additional rotation axis running in a transverse direction.

In one embodiment, an arched guide for supporting the x-ray detector on the retaining column is provided to move the x-ray detector about the longitudinal axis. An arched guide may provide circular movement about the first longitudinal axis and may be efficient and economical.

In another embodiment, the arched guide is coupled, for example, by way of a base element, to a positioning carriage, which can be moved along the retaining column. A swivel joint may be provided between the base element and the positioning carriage to rotate the base element about the transverse axis. The positioning carriage may execute the vertical movement of the detector along the retaining column. At the same time, the base element serves to couple the arched guide to the positioning carriage and/or retaining column. To realize the rotational movement of the detector element about the transverse axis, the swivel joint for rotating the x-ray detector may be attached between the base element and the positioning carriage.

The mobility or repositioning options for the x-ray detector may be extended. For example, in one preferred development, the x-ray detector may supported on the repositioning mechanism in such a manner that the x-ray detector may be rotated about a second longitudinal axis. The x-ray detector may be supported on the arched guide in such a manner that the x-ray detector can be rotated about the second rotation axis. This introduces a third degree of rotation of the x-ray detector, whereby the rotation axis runs through the connecting point configured as a swivel joint between the x-ray detector and the arched rail and extends in the longitudinal direction of the patient support. Such a swivel movement is advantageous, if the x-ray detector is located on the end of the arched rail, where the freedom of movement is less restricted by the rail and where the x-ray detector can assume a number of positions during the swivel movement. The x-ray detector may be swiveled through at least 90° between a horizontal and a vertical position.

In one embodiment, the retaining column may be coupled mechanically to the patient support and supported in such a manner that patient support can be repositioned in relation to the retaining column. Accordingly, the retaining column and also the x-ray detector are supported indirectly on the support unit. The retaining column is coupled mechanically to a support case for the patient support, which is supported by the support arm.

An x-ray emitter may be disposed on the side of the patient support facing away from the x-ray detector, being likewise coupled mechanically to the patient support, in particular to the support case. This embodiment is characterized by particularly good utilization of space and also requires little outlay when controlling a simultaneous movement of the patient support and the x-ray detector.

To ensure unimpeded access to the patient support, the x-ray detector or x-ray emitter, the support arm may be moved vertically on the support unit.

The adjustment and alignment options for the components of the x-ray apparatus are also increased in that the support arm on the support unit may be rotated about a rotation axis that extends in a transverse direction. Thus a patient supported on the patient support may be moved to an alignment favorable for the treatment or examination. The rotational movement may be used to move the patient support into a vertical (park) position.

The patient support may be supported in such a manner that the patient support may be repositioned in relation to the support arm. To position the patient correctly, when the x-ray detector and x-ray emitter are stationary, the patient support can be moved in the longitudinal and/or transverse direction. Repositioning of the patient support in relation to the support arm is effected by way of the support case, on which the patient support executes a sort of sliding movement during repositioning.

To allow a patient to be examined on a number of sides from a number of directions by the x-ray apparatus, an x-ray emitter is provided that is decoupled from the support arm. The x-ray emitter may be configured, for example, to be suspended from a ceiling or, alternatively, may be secured to the floor or a wall. The high degree of flexibility of alignment of the x-ray detector allows recordings to be taken of the patient, in which the patient is irradiated from the side or from above, for example.

A method for repositioning an x-ray apparatus according to the above embodiments may be provided. The patient support may be positioned in a vertical position by way of the support arm and the x-ray detector may be rotated about the transverse axis in such a manner that a detector recording plane is aligned horizontally.

In a first act, the patient support is positioned in the vertical position by swiveling the support arm so that the patient can be examined next to it in a "standing" position. The retaining column with the x-ray detector is then rotated about the transverse axis so that the recording plane of the detector is horizontal and facing upward. As a result, a fluoroscopy recording or static recording of the hand of the patient, for example, may be taken. The hand may be positioned above the detector recording plane. The versatile repositioning options of the x-ray apparatus, which make it suitable both for static recordings and also for dynamic x-ray imaging, create a combined device, thereby reducing costs and the space requirement.

DETAILED DESCRIPTION

Figure 1:
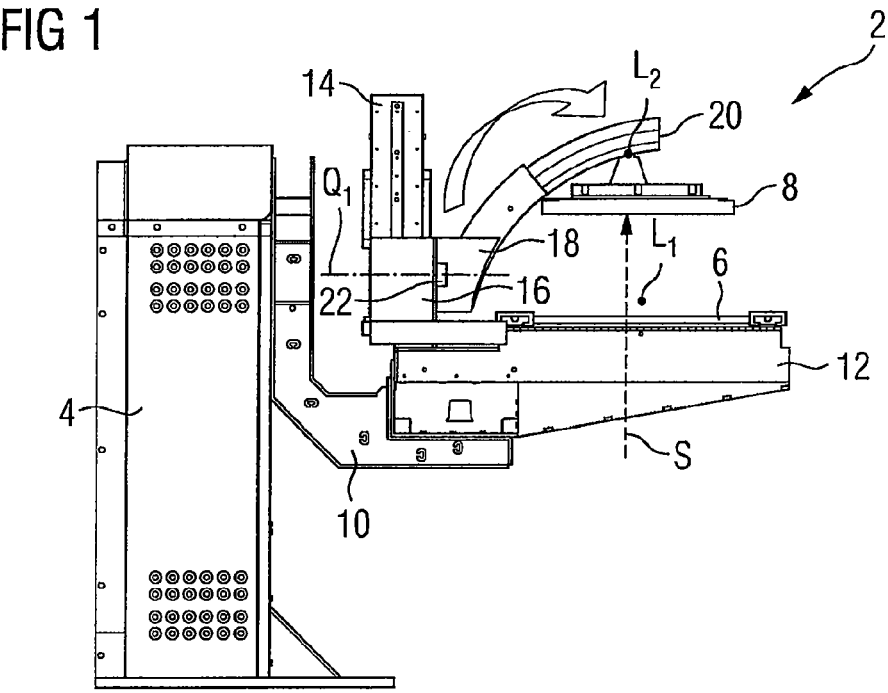
FIG. 1 shows one embodiment of an x-ray apparatus with an x-ray detector disposed above a patient support.

Parts with identical action are shown with identical reference characters in all the figures.

Figure 2:
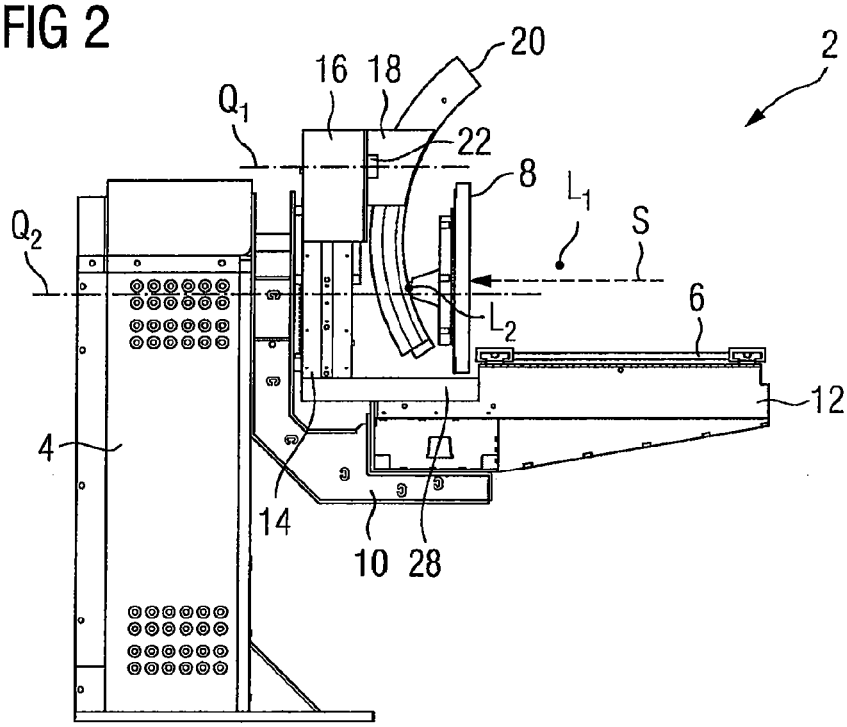
FIG. 2 shows the x-ray apparatus according to FIG. 1 with the x-ray detector in a lateral position.

FIGS. 1 and 2 show an x-ray apparatus (system) 2, which comprises a support unit 4, a patient support 6 and an x-ray detector 8. The support unit 4 is a column and is fixed to the floor. The patient support 6 is supported on the support unit 4 in such a manner that it can be repositioned by way of a support arm 10. The x-ray detector is supported on the support arm 10 by way of a repositioning mechanism with a number of degrees of freedom of movement. A retaining column 14 for the x-ray detector 8 is supported on a support case 12 of the patient support 6. The retaining column 14 has a positioning carriage 16, which can be moved up and down along the retaining column 14 perpendicular to the patient support 6. The positioning carriage 16 is coupled mechanically to a base element 18, on which an arched guide 20 is disposed. The arched guide 20 may be repositioned in relation to the base element 18. The arched guide 20 serves to support the x-ray detector 8 in such a manner that the x-ray detector 8 can be moved along the guide 20. During the movement along a curved path defined by the guide 20, the x-ray detector 8 describes an arc about a first longitudinal axis $L_1$, which extends perpendicular to the plane of the drawing and is shown by a dot. The first longitudinal axis $L_1$ extends in the longitudinal direction of the horizontally positioned patient support 6 and is located between the patient support 6 and the x-ray detector 8 disposed above it.

Figure 3:
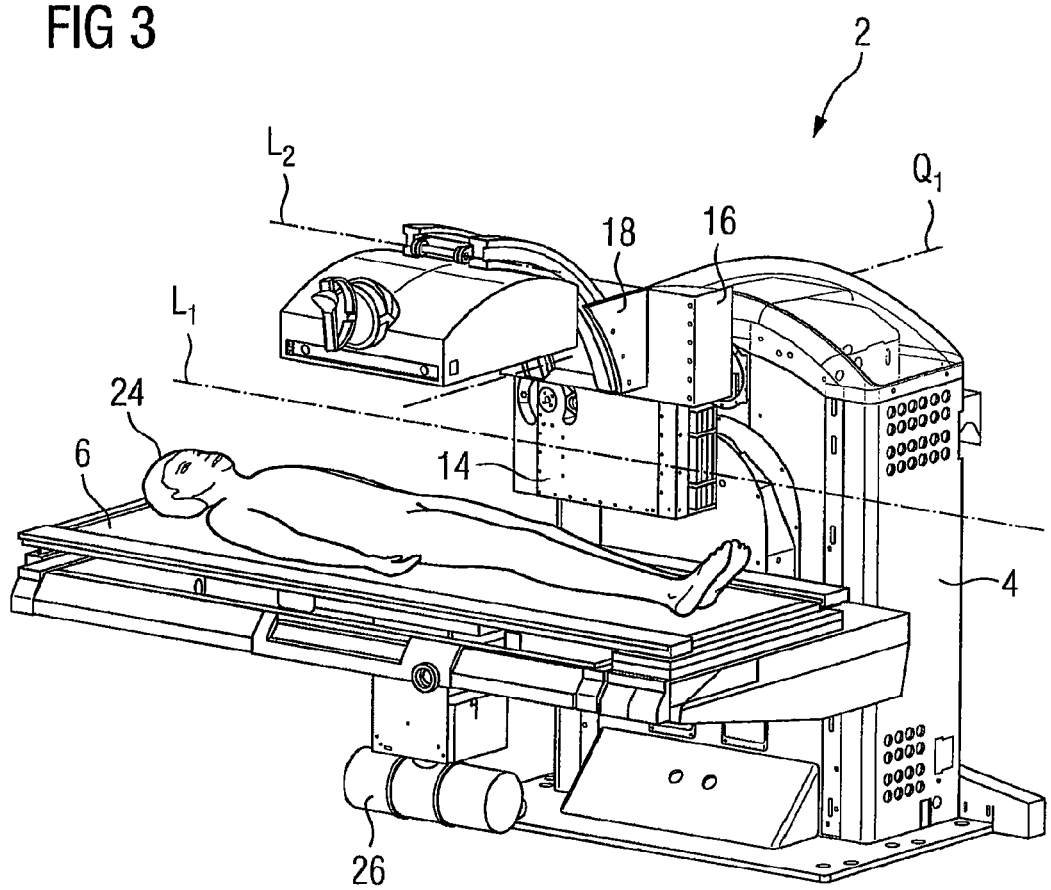
FIG. 3 shows one embodiment of an x-ray apparatus with a patient supported on a patient support.

A swivel joint 22 is also provided between the positioning carriage 16 and the base element 18, so that base element 18 and thus the detector 8 can rotate about a transverse axis $Q_1$ running through the swivel joint 22, which extends in the transverse direction of the patient support 6. Being supported by way of the arched guide 20 and the retaining column 14 on the support case 12 of the patient support 6 the x-ray detector 8 is thus able to be rotated in relation to the patient support 6 both about the longitudinal axis $L_1$ and about the transverse axis $Q_1$. As a result the x-ray detector 8 can be moved from a position above the patient support 6, as shown in FIG. 1, about the first longitudinal axis $L_1$ into a lateral position to the side of the patient support 6, as shown in FIG. 2, without a patient 24 lying on the patient support 6 having to be moved. In the first position, the x-ray apparatus 2 is suitable for recording the patient 24 from below. This is shown in FIG. 3. The patient 24 is irradiated from below with an x-ray emitter 26 disposed below the patient support 6. The radiation direction being shown by the arrow S in FIG. 1 and FIG. 2. In the exemplary embodiment shown the x-ray emitter 26 is likewise coupled mechanically to the patient support 6 and thus supported by the support arm 10.

In addition to a rotation of the x-ray detector 8 about the longitudinal axes $L_1$ and $L_2$ and the transverse axis $Q_1$ and the capacity for vertical repositioning along the retaining column 14, the x-ray apparatus 2 is characterized by numerous other movement options for the components, so that all known applications of an x-ray device, such as dynamic fluoroscopy and static recording, of a prone or standing patient, are possible with the x-ray apparatus 2. As a result, the retaining column 14 may be coupled in a movable manner to the support case 12 of the patient support 6 and can be moved in a longitudinal and transverse direction of the patient support 6. Displacement of the retaining column 14 with the x-ray detector 8 in a transverse direction is shown by the comparison of FIGS. 1 and 2, for example. As shown in FIG. 2, the retaining column 14 is moved backward in the direction of the support unit 4 with the aid of a guide rail 28, so that there is sufficient space available for the patient 24 when the x-ray detector 8 is in the lateral position.

To reposition the described x-ray detector 8, a multi-part repositioning mechanism is provided, which includes the retaining column 14, the positioning carriage 16, the base element 18, the arched guide 20, the swivel joint 22 and the mechanism included in the base element 18 to reposition the arched guide 20 in relation to the base element 18. The guide rail 28 and other means (not shown in detail here) in the support case for displacing the retaining column 14 can also be considered to be parts of the repositioning mechanism.

The patient support 6 may be displaced in a linear manner in the longitudinal and transverse directions, for example, by sliding over the support case 12, so that the patient support 6 is supported in such a manner that it can be repositioned in relation to the support arm 10.

The support arm 10 may be supported in a repositionable manner on the support unit 4. The support arm 10 may be moved in a vertical direction or can be rotated about a rotation axis $Q_2$, which extends in a transverse direction of the patient support 6.

Figure 4:
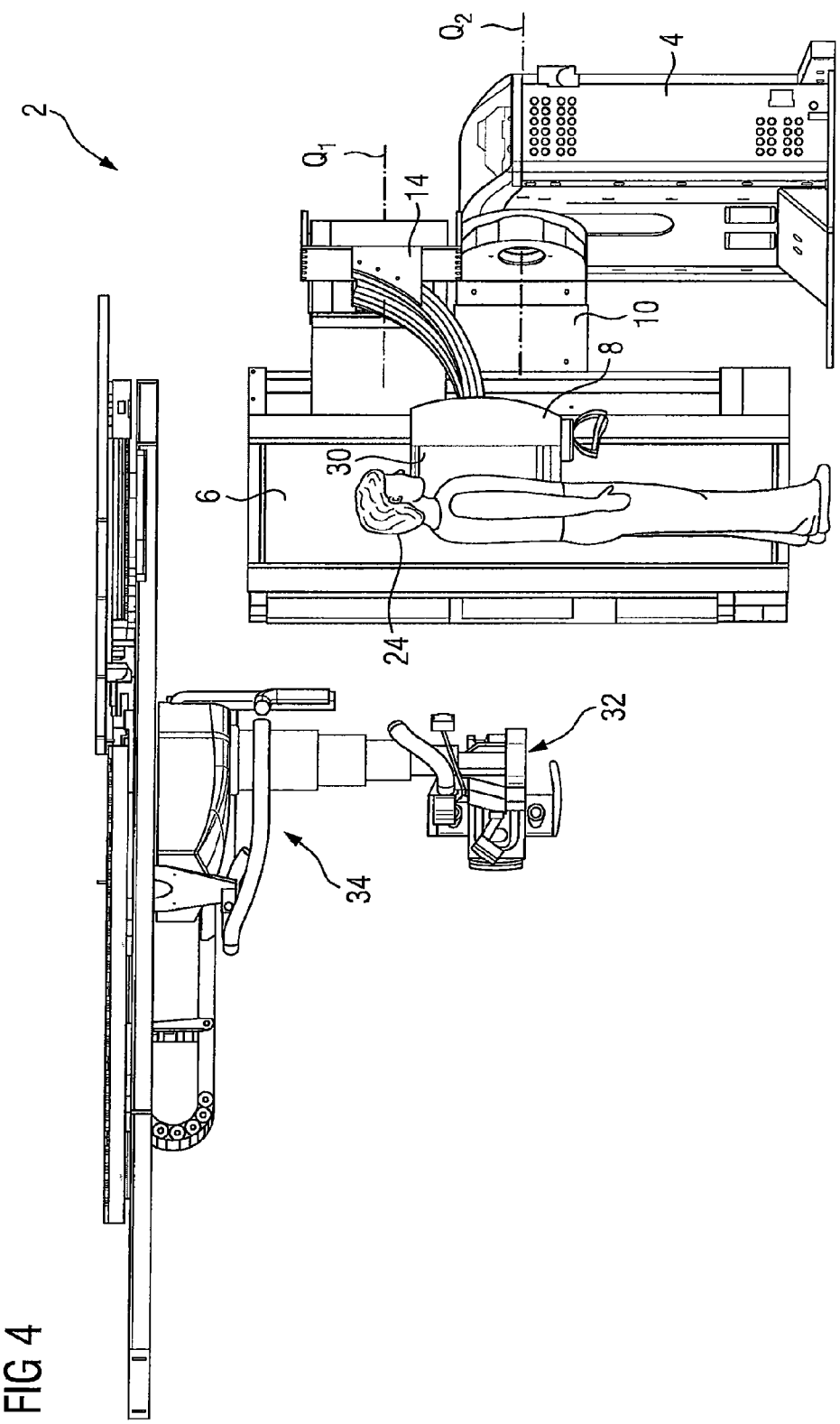
FIG. 4 shows the x-ray apparatus according to FIG. 3 with a vertically positioned patient support and with an additional x-ray emitter.
Figure 5:
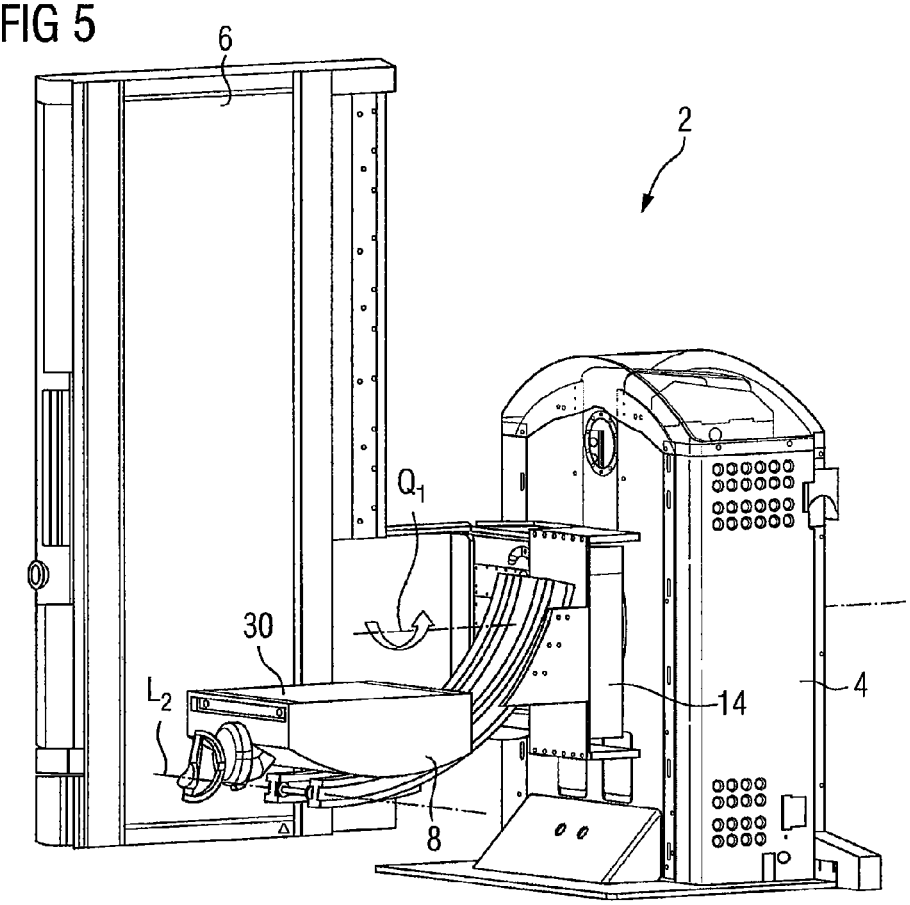
FIG. 5 shows the x-ray apparatus according to FIG. 3, with a recording plane of the x-ray detector aligned horizontally facing upward.

Two different applications of the x-ray apparatus 2 are shown in FIGS. 4 and 5. According to FIG. 4, the x-ray apparatus 2 is moved into a position, which is particularly suitable for fluoroscopy, for example, of the lungs on the standing patient 24. To align the x-ray apparatus 2 in the position shown, the patient support 6 may be rotated through 90° by way of the support arm 10 about the rotation axis $Q_2$, so that the patient support 6 is positioned in a vertical position. The x-ray detector 8 may be rotated about the first transverse axis $Q_1$ likewise through 90° and aligned in such a manner that a detector recording plane 30 is no longer disposed parallel to the patient support 6 but is disposed perpendicular to the patient support 6.

A second x-ray emitter 32, which is decoupled from the support unit 4, may be used to take a fluoroscopy recording of the patient 24. In the exemplary embodiment shown the x-ray emitter 32 is suspended from a ceiling by way of a ceiling gantry 34 and its position is correlated with that of the x-ray apparatus 2. The movement of the x-ray emitter 32 may be decoupled from that of the patient support 6 and the x-ray detector 8. However, the position is known at all times, at least in relation to the x-ray detector 8. The x-ray emitter 32 may be disposed in such a manner that there is sufficient space between the x-ray emitter 32 and the x-ray detector 8, so that the patient 24 can be positioned near the x-ray detector 8 so that good quality recordings can be taken and at the same time there is a big gap between the x-ray emitter 32 and the x-ray detector 8.

Starting from the arrangement according to FIG. 4, the x-ray apparatus 2 is moved into the position shown in FIG. 5, by moving the retaining column 14 vertically downward and swinging the x-ray detector 8 upward through 90° about the second longitudinal axis $L_2$, so that the detector recording plane 30 is aligned horizontally facing upward. In the position of the x-ray detector 8, shown in FIG. 5, it is possible, for example, to take a static recording of a hand of a patient 24 with the aid of the x-ray apparatus 2. The second x-ray emitter 32, which is suspended from the ceiling and decoupled from the support unit 4, may be used for the static recording of the hand.

The exemplary embodiments shown in FIGS. 3, 4, and 5 show three different applications of the x-ray unit 2. As can be seen from the figures, the x-ray unit 2 is suitable both for dynamic fluoroscopy recordings to visualize processes taking place in the body of the patient 24 and also for static images of parts of the body of the patient 24, who can be positioned differently and be irradiated from a number of directions.

Figure 6:
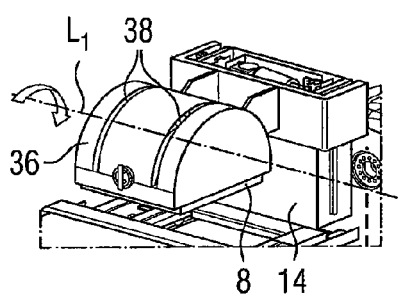
FIG. 6 shows an alternative embodiment of the movement mechanism of an x-ray detector.
Figure 7:
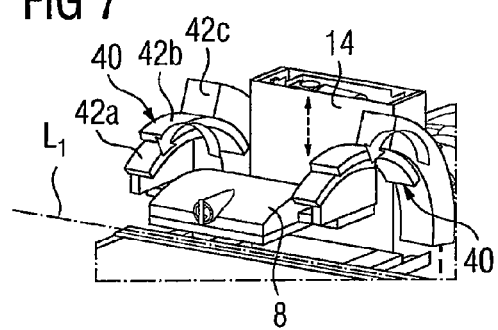
FIG. 7 shows another alternative embodiment of the movement mechanism of an x-ray detector.

FIGS. 6 and 7 show two further variants of the repositioning options for a detector 8. As shown in FIG. 6, the detector 8 is held by a semi-cylindrical housing 36, on which rails 38 are disposed for the rotational repositioning of the housing 36 and of the detector 8. The detector 8 may be guided in an arched manner about a longitudinal axis $L_1$, which runs through the x-ray detector 8. The detector 8 can also be moved at least in a vertical direction by a multi-part repositioning mechanism. The detector 8 may be repositioned in a linear manner in a longitudinal and transverse direction in relation to a patient support.

The x-ray detector 8 according to FIG. 7 is held on both sides by two curved arms 40 and when moved describes a circle (e.g., moved in a circle) about the first longitudinal axis $L_1$, which runs outside the x-ray detector 8. Each of the curved arms 40 in this exemplary embodiment has three curved parts 42a, 42b, 42c that can be repositioned in relation to one another and can be extended telescopically. The x-ray detector 8 is on the one hand embodied so that it can be rotated in relation to the curved arms 40 and on the other hand it can be repositioned in relation to a patient support by way of the curved arms 40. The arrangement also has a repositioning mechanism, which is similar in structure to the one according to the first embodiment of the x-ray apparatus 2 described above.

The invention claimed is:

1. An x-ray apparatus comprising:
a support unit having a support arm;
an x-ray detector supported on the support arm, the x-ray detector being a solid-state detector; and
a patient support supported on the support unit in such a manner that the patient support is repositionable by the support arm, the x-ray detector being configured to move perpendicularly to the patient support by a retaining column of a repositioning mechanism and to rotate relative to the patient support about a first longitudinal axis extending in a longitudinal direction of the patient support,
wherein the x-ray detector is configured to rotate relative to the patient support about a transverse axis extending in a transverse direction of the patient support.

2. The x-ray apparatus as claimed in claim 1, wherein the x-ray detector is configured to be moved along a curved path about the first longitudinal axis.

3. The x-ray apparatus as claimed in claim 2, further comprising an arched guide for moving the x-ray detector about the first longitudinal axis, the arched guide being provided on the retaining column to support the x-ray detector.

4. The x-ray apparatus as claimed in claim 3, wherein the arched guide is coupled by way of a base element to a positioning carriage, the positioning carriage being movable along the retaining column, with a swivel joint being provided between the base element and the positioning carriage to rotate the base element about the transverse axis.

5. The x-ray apparatus as claimed in claim 2, wherein the x-ray detector is supported on an arched guide in such a manner that the x-ray detector is rotatable about the transverse axis.

6. The x-ray apparatus as claimed in claim 1, wherein the x-ray detector is supported on the repositioning mechanism.

7. The x-ray apparatus as claimed in claim 1, wherein the retaining column is coupled mechanically to the patient support and is supported in such a manner that the retaining column is repositionable in relation to the patient support.

8. The x-ray apparatus as claimed in claim 1, further comprising an x-ray emitter disposed on a side of the patient support facing away from the x-ray detector, the x-ray emitter being coupled mechanically to the patient support.

9. The x-ray apparatus as claimed in claim 1, wherein the support arm is configured to be moved vertically on the support unit.

10. The x-ray apparatus as claimed in claim 1, wherein the support arm is configured to be rotated about a rotation axis that extends in a transverse direction.

11. The x-ray apparatus as claimed in claim 1, wherein the patient support is supported in such a manner that the patient support can he repositioned in relation to the support arm.

12. The x-ray apparatus as claimed in claim 1, further comprising an x-ray emitter that is decoupled from the support unit.

13. A method for repositioning an x-ray apparatus, the method comprising:
   supporting an x-ray detector on a support arm of a support unit;
   supporting a patient support on the support unit;
   positioning the patient support with the support arm in a vertical position;
   moving the x-ray detector perpendicularly to the patient support by a retaining column of a repositioning mechanism;
   rotating the x-ray detector, relative to the patient support, about a first longitudinal axis extending in a longitudinal direction of the patient support: and
   rotating the x-ray detector, relative to the patient support, about a transverse axis extending in a transverse direction of the patient support in such a manner that a detector recording plane is aligned horizontally.

* * * * *